(12) United States Patent
Ferrer

(10) Patent No.: US 11,759,586 B1
(45) Date of Patent: Sep. 19, 2023

(54) NASAL SPRAY BOTTLE WITH IMPROVED NOZZLE AND SYSTEM OF APPLICATION

(71) Applicant: FERRER MEDICAL INNOVATIONS, LLC, Hallandale Beach, FL (US)

(72) Inventor: Gustavo Ferrer, Hallandale Beach, FL (US)

(73) Assignee: FERRER MEDICAL INNOVATIONS, LLC, Hallandale Beach, FL (US)

( * ) Notice: Subject to any disclaimer, the term of this patent is extended or adjusted under 35 U.S.C. 154(b) by 0 days.

(21) Appl. No.: 17/720,251

(22) Filed: Apr. 13, 2022

(51) Int. Cl.
*B05B 11/00* (2023.01)
*A61M 15/08* (2006.01)

(52) U.S. Cl.
CPC ......... *A61M 15/08* (2013.01); *B05B 11/0005* (2013.01); *A61M 2205/586* (2013.01)

(58) Field of Classification Search
CPC ............ A61M 15/08; A61M 2205/586; B05B 11/0005
See application file for complete search history.

(56) References Cited

U.S. PATENT DOCUMENTS

| 6,092,692 A * | 7/2000 | Riskin ............... A61M 15/0073 222/23 |
| 6,189,739 B1 * | 2/2001 | von Schuckmann ........................ B05B 11/1004 222/321.6 |
| 2004/0004138 A1 * | 1/2004 | Hettrich .............. B05B 11/0044 239/569 |
| 2011/0066136 A1 * | 3/2011 | Moller ................... A61M 11/08 604/514 |

FOREIGN PATENT DOCUMENTS

| AU | 2011266100 B2 * | 4/2015 | ............. B05B 1/341 |
| FR | 2739294 A1 * | 4/1997 | .......... A61M 11/007 |
| KR | 20170023089 * | 3/2017 | ............ A61M 11/06 |

* cited by examiner

*Primary Examiner* — Bob Zadeh
(74) *Attorney, Agent, or Firm* — ALBERT BORDAS, P.A.

(57) ABSTRACT

A nasal spray bottle with improved nozzle, which has a cap assembly, a nozzle assembly having a flap guidance, a bottle coupling assembly, a dispenser mechanism, and a bottle assembly. The nozzle assembly couples to the bottle coupling assembly, the bottle coupling assembly mounts onto the bottle assembly, and the dispenser mechanism is inside along the nozzle assembly, the bottle coupling assembly, and the bottle assembly. The flap guidance has first and second transversal edges, first and second longitudinal edges, and a central edge. The flap guidance is fixedly attached around the nozzle body by the central edge. The flap guidance is oval shaped. The flap guidance is attached around the nozzle body defining a predetermined angle.

16 Claims, 6 Drawing Sheets

NASAL SPRAY BOTTLE WITH IMPROVED NOZZLE AND SYSTEM OF APPLICATION

BACKGROUND OF THE INVENTION

Field of the Invention

The present invention relates to nasal spray bottles, and more particularly, to nasal spray bottles with improved nozzles and systems of application.

Description of the Related Art

Applicant is not aware of any nasal spray bottle with an improved nozzle having the novel features of the present invention.

SUMMARY OF THE INVENTION

The present invention is a nasal spray bottle with improved nozzle, comprising a cap assembly, a nozzle assembly having a flap guidance, a bottle coupling assembly, a dispenser mechanism, and a bottle assembly. The nozzle assembly couples to the bottle coupling assembly, the bottle coupling assembly mounts onto the bottle assembly, and the dispenser mechanism is inside along the nozzle assembly, the bottle coupling assembly, and the bottle assembly.

The cap assembly comprises a cap upper section, a cap lower section, a bottom end, and a top end. The nozzle assembly further comprises a nozzle body, actuator tabs, and a lower wall. The nozzle body comprises a nozzle top end and a nozzle bottom end, whereby the nozzle top end comprises an orifice.

The flap guidance comprises first and second transversal edges, first and second longitudinal edges, and a central edge. The flap guidance is fixedly attached around the nozzle body by the central edge. The flap guidance is oval shaped. The flap guidance is attached around the nozzle body defining a predetermined angle. The first transversal edge approximately aligns with the nozzle bottom end and the second transversal edge is separated a predetermined distance from the nozzle bottom end toward the nozzle top end. The predetermined angle is between about 30 and 60 degrees respect to a bottle bottom base. The flap guidance allows a user to orientate the nozzle body in a predetermined application angle between about 12 to 45 degrees.

The bottle coupling assembly comprises a coupling upper wall, a coupling lower wall, a bottom end, an internal wall having a top wall defining a hole, a chaplet, and a gasket. The bottom end defines a lower lip and the coupling upper wall with the internal wall define an elongated channel, which receive the lower wall. The chaplet is inside the internal walls and the gasket is below the chaplet.

The dispenser mechanism comprises an inner stem, an external stem to create a swirling effect, a lower stem, a sub-stem, first and second springs, a piston, a housing, a ball, and a tube. The housing houses the sub-stem, the first and second springs, the piston, and the ball. The chaplet receives the housing and the tube protrudes from the housing toward the bottle bottom base.

The bottle assembly comprises a bottle neck, a bottle top end, external threads, a neck tab, and a bottle body. The coupling lower wall comprises internal threads to receive the external threads and the gasket is positioned between the chaplet and the bottle top end.

A method of using the nasal spray bottle with improved nozzle comprising the steps of:

A) positioning a head of a user in approximately 90 degrees;
B) placing the nozzle body at an application angle between about 12 and 45 degrees to the head;
C) introducing the nozzle body approximately 1.5 cm inside a nostril of the user;
D) squeezing the spray bottle by pressing the actuator tabs 2 times into each nostril.

The spray plume geometry angle of dispersions is between about 73.3 to 80.5 degrees.

The nozzle body is placed in the application angle between about 12 and 15 degrees for the treatment of viral diseases and vaccines applications. In a preferred embodiment, the nasal spray bottle is placed in an application angle of approximately 15 degrees for the treatment of viral diseases and vaccines applications, and approximately 45 degrees for the treatment of allergic rhinitis.

It is therefore one of the main objects of the present invention to provide a nasal spray bottle with improved nozzle.

It is another object of this invention to provide a nasal spray bottle with improved nozzle, which has a flap guidance.

It is another object of this invention to provide a nasal spray bottle with improved nozzle, which has a flap guidance defining a predetermined angle.

It is another object of this invention to provide a nasal spray bottle with improved nozzle that is volumetrically efficient for carrying, transporting, and storage.

It is another object of this invention to provide a nasal spray bottle with improved nozzle that can be readily assembled and disassembled without the need of any special tools.

It is another object of this invention to provide a nasal spray bottle with improved nozzle, which is of a durable and reliable construction.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE INVENTION

Figure 1:
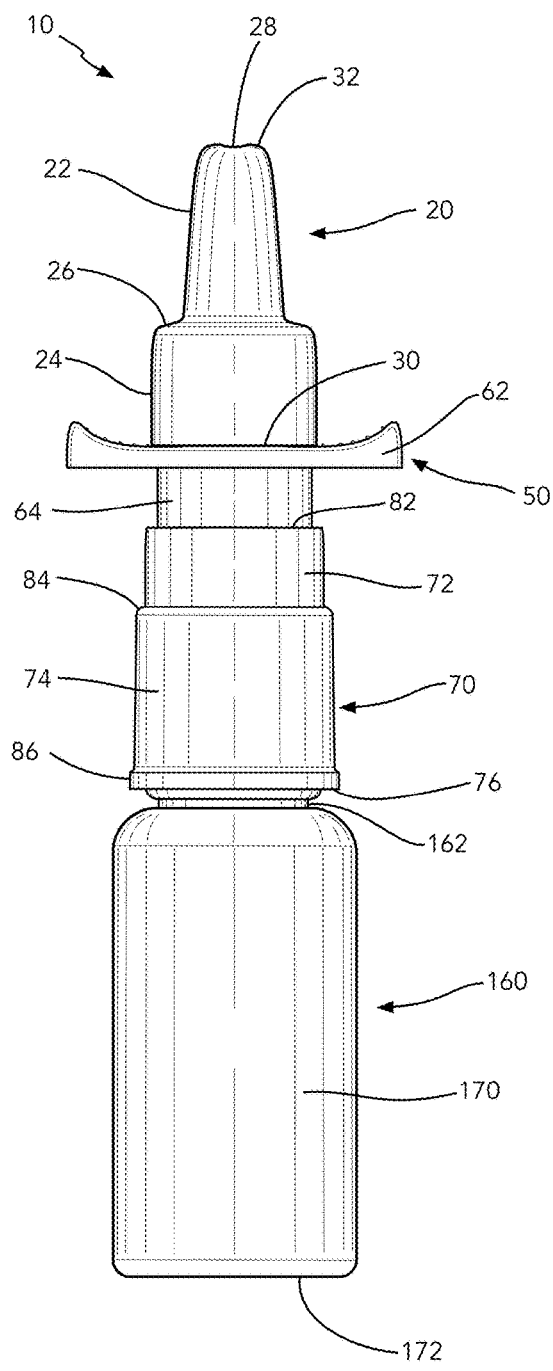
FIG. 1 is a front view of the present invention.

Referring now to the drawings, the present invention is a nasal spray bottle with an improved nozzle and is generally referred to with numeral 10. It can be observed that it basically includes cap assembly 20, nozzle assembly 50, bottle coupling assembly 70, dispenser mechanism 120, and bottle assembly 160.

Figure 2:
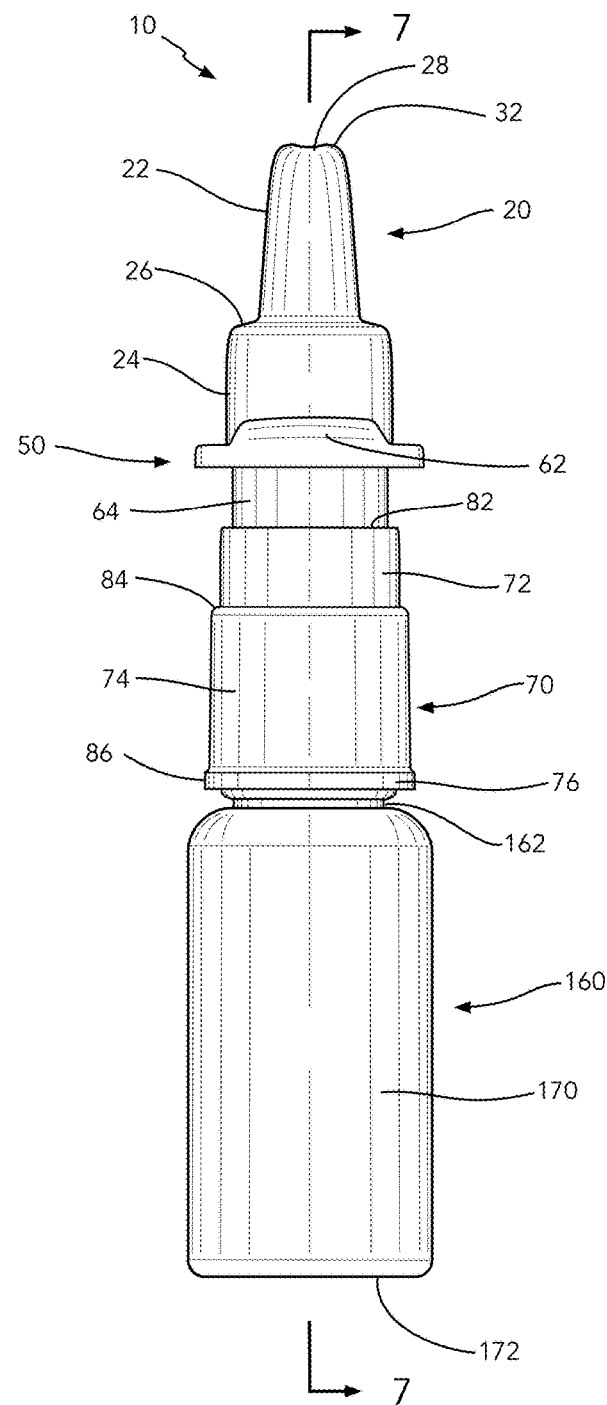
FIG. 2 is a side view of the present invention.

As seen in FIGS. 1 and 2, nozzle assembly 50 is connected to bottle coupling assembly 70, and bottle coupling assembly 70 mounts onto bottle assembly 160. Nozzle assembly 50 receives cap assembly 20.

Cap assembly 20 comprises cap upper section 22, cap lower section 24, bottom end 30, and top end 32. Top end 32 may comprise indent 28. Cap assembly 20 may further comprise middle wall 26 between cap upper section 22 and cap lower section 24.

Bottle coupling assembly 70 comprises coupling upper wall 72, coupling lower wall 74, and bottom end 76. Coupling upper wall 72 comprises top end 82. Coupling upper wall 72 and coupling lower wall 74 define lip 84.

Figure 3:
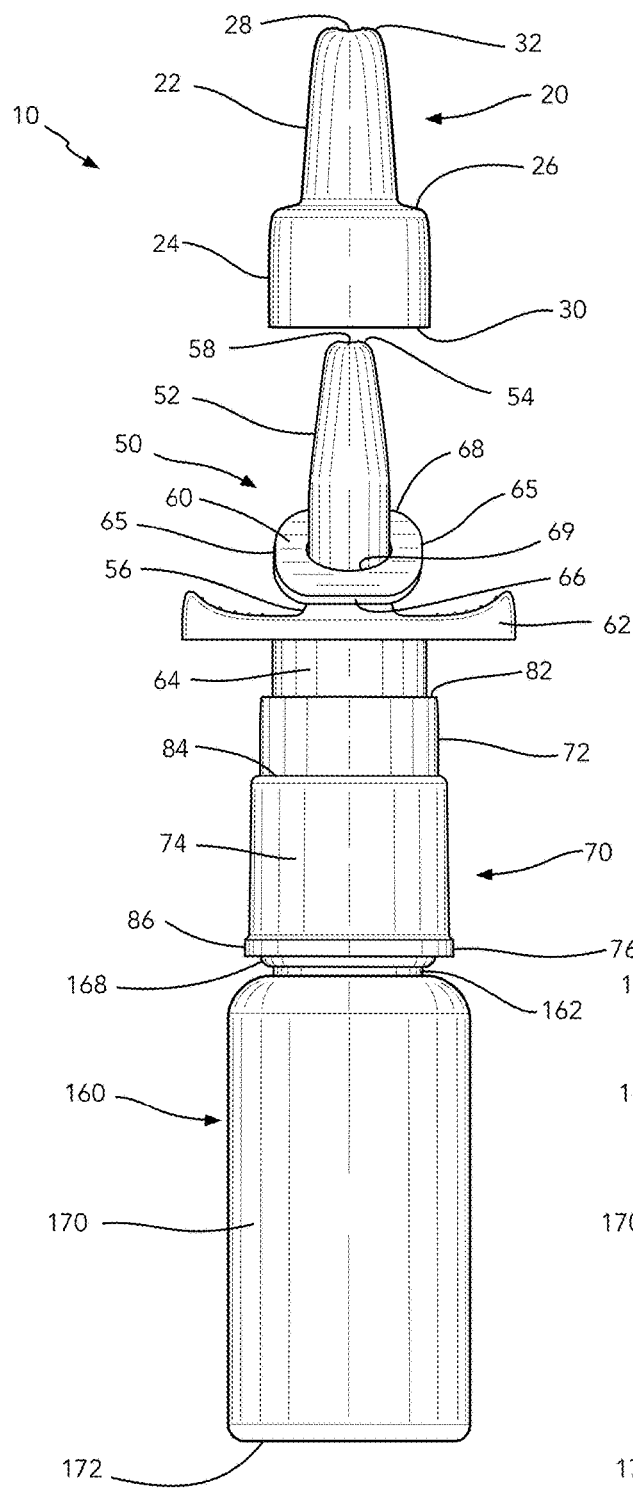
FIG. 3 is a front view of the present invention having a cap separated showing a nozzle.
Figure 4:
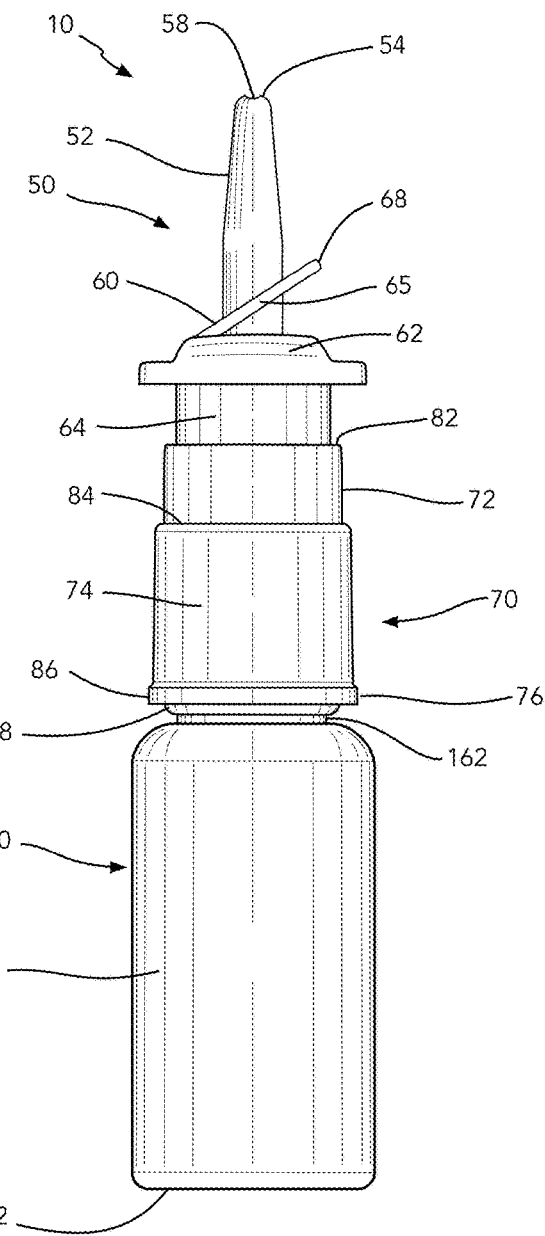
FIG. 4 is a side view of the present invention without the cap.

As seen in FIGS. 3 and 4, nozzle assembly 50 comprises nozzle body 52, flap guidance 60, actuator tabs 62, and lower wall 64. Nozzle body 52 comprises nozzle top end 54 and nozzle bottom end 56, whereby nozzle top end 54 comprises orifice 58.

Figure 5:
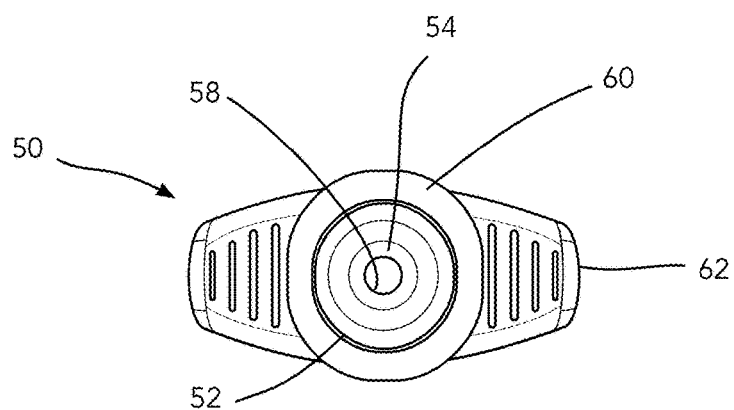
FIG. 5 is a top view of a nozzle assembly of the present invention.
Figure 6:
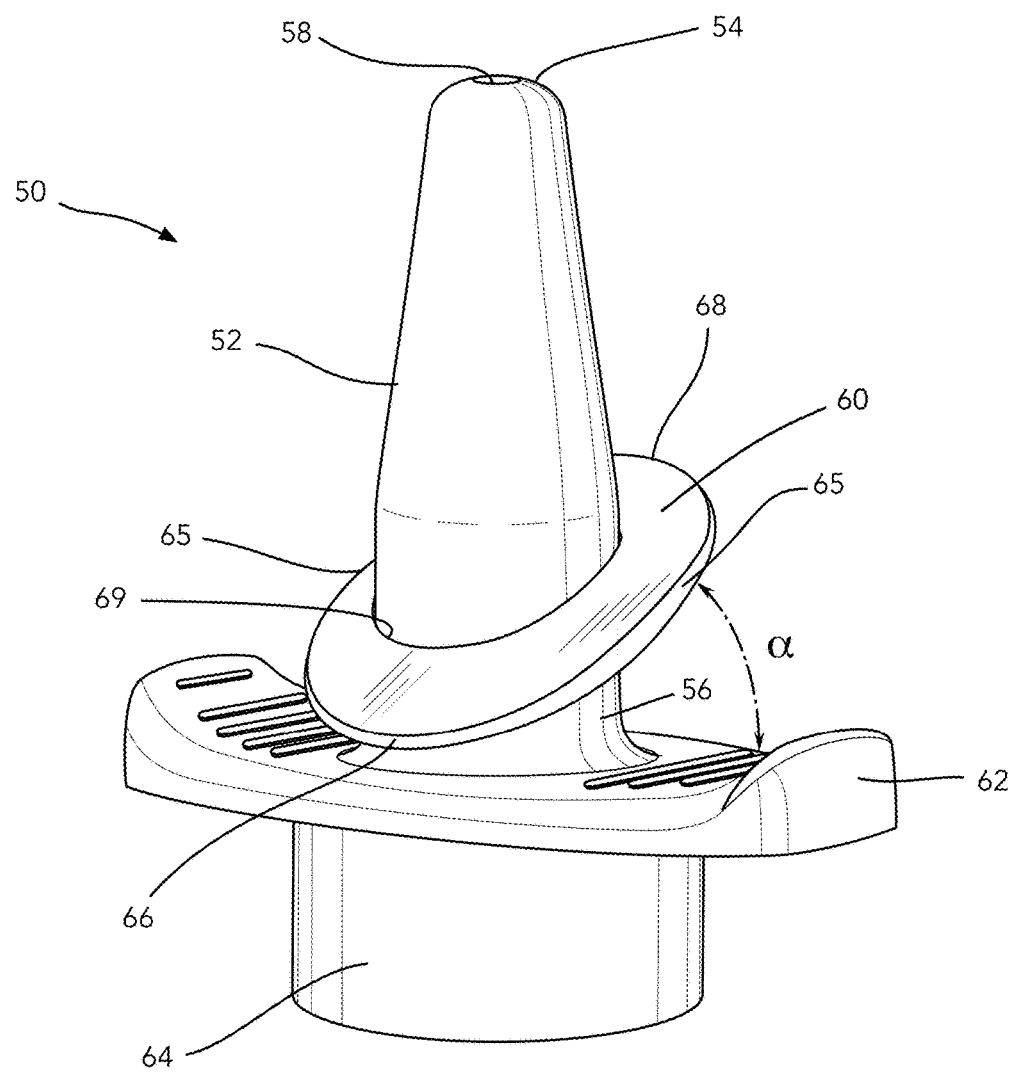
FIG. 6 is an isometric view of a nozzle assembly of the present invention.
Figure 7:
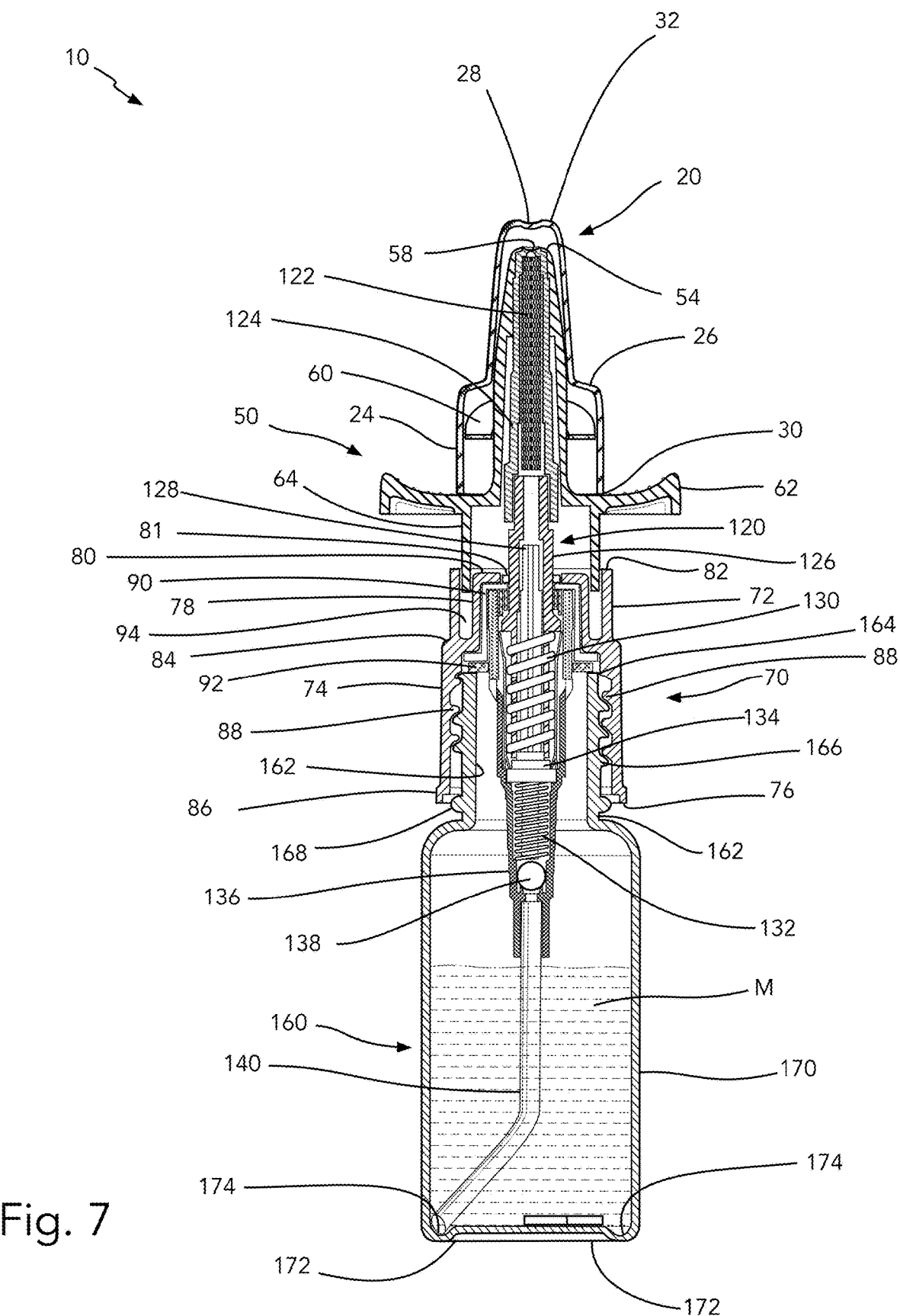
FIG. 7 is a cut view taken along lines 7-7 from FIG. 2.

As seen in FIGS. 5 and 6, flap guidance 60 is positioned around nozzle body 52. Flap guidance 60 comprises first and second longitudinal edges 65, first and second transversal edges 66 and 68, and central edge 69. In a preferred embodiment, flap guidance 60 is oval shaped.

Flap guidance 60 is fixedly attached around nozzle body 52 by central edge 69. Flap guidance 60 is attached around nozzle body 52 defining predetermined angle α. First transversal edge 66 approximately aligns with nozzle bottom end 56, and second transversal edge 68 is separated a predetermined distance from nozzle bottom end 56 toward nozzle top end 54. The predetermined angle α defined by flap guidance 60 is between about 30 and 60 degrees with respect to bottle bottom base 172, seen in FIG. 4. In a preferred embodiment, flap guidance 60 defines angle α of approximately 60 degrees with respect to actuator tabs 62.

Figure 8A:
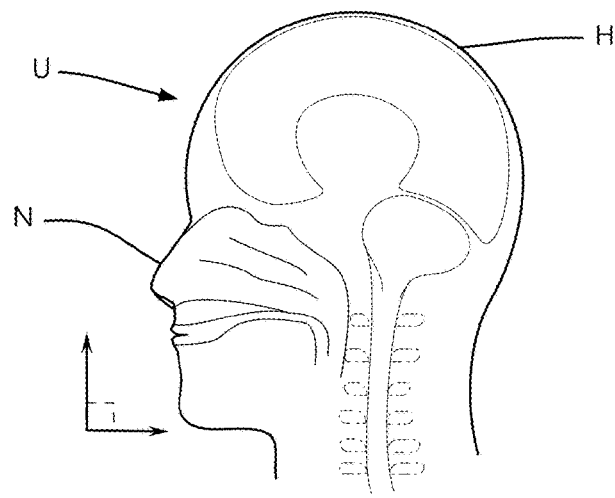
FIG. 8A is a representation of a first step of a method of using the present invention.
Figure 8B:
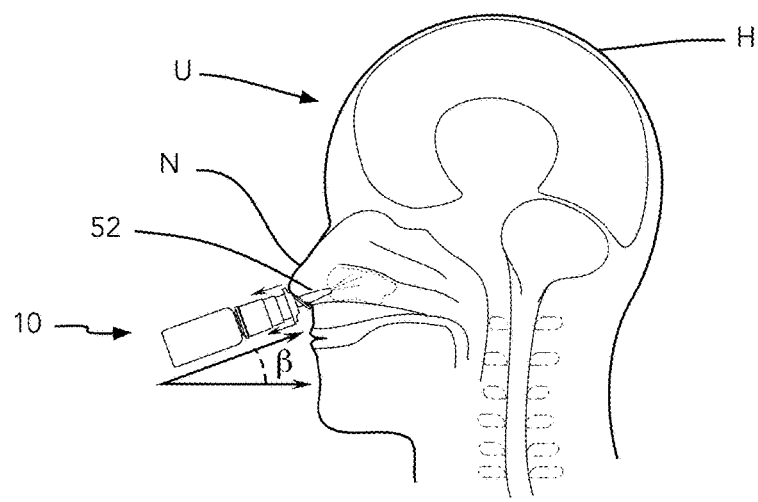
FIG. 8B is a representation of a second step of the method of using the present invention showing a first embodiment having a first predetermined application angle.
Figure 8C:
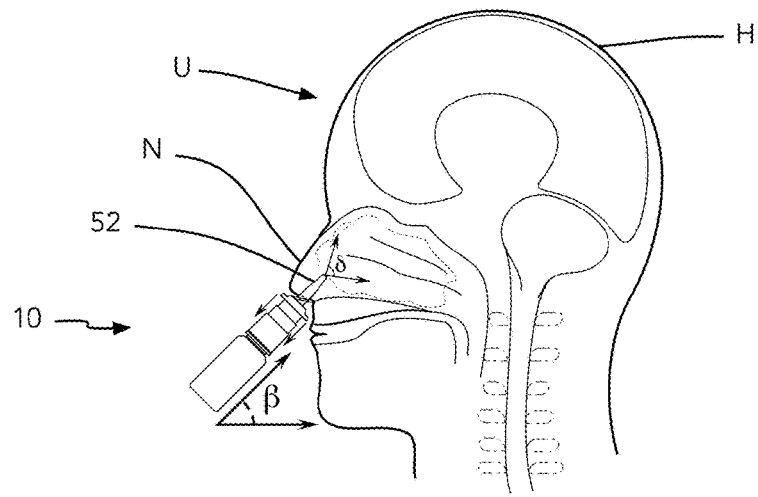
FIG. 8C is a representation of a third step of the method of using the present invention showing a second embodiment having a second predetermined application angle.

Flap guidance 60 allows user U to orientate nozzle body 52 to a predetermined application angle β between about 12 to 45 degrees, as seen in FIGS. 8B and 8C.

Nozzle assembly 50 is configured with a plume geometry swirling effect that delivers angle of dispersion δ between about 73.3 to 80.5 degrees.

As seen in FIG. 7, dispenser mechanism 120 is inside along nozzle assembly 50, bottle coupling assembly 70, and bottle assembly 160.

Bottle coupling assembly 70 further comprises internal wall 78 having top wall 80 defining hole 81. Bottle coupling assembly 70 further comprises chaplet 90 and gasket 92. Bottom end 76 defines lower lip 86. Coupling upper wall 72 and internal wall 78 define elongated channel 94. Chaplet 90 is inside internal walls 78, and gasket 92 is below chaplet 90. Elongated channel 94 receives lower wall 64.

Dispenser mechanism 120 comprises inner stem 122, external stem 124, lower stem 126, sub-stem 128, first and second springs 130 and 132, piston 134, housing 136, ball 138, and tube 140. Housing 136 houses sub-stem 128, first and second springs 130 and 132, piston 134, and ball 138. Chaplet 90 receives housing 136, and tube 140 protrudes from housing 136 toward bottle bottom base 172.

Bottle assembly 160 comprises bottle neck 162, bottle top end 164, external threads 166, neck tab 168, and bottle body 170.

Coupling lower wall 74 comprises internal threads 88 to receive external threads 166. Gasket 92 is positioned between chaplet 90 and bottle top end 164. In a preferred embodiment, bottle bottom base 172 comprises bottom indents 174. Lower lip 86 receives neck tab 168.

Nozzle body 52 receives external stem 124 having inner stem 122 designed to create a swirling effect. Lower stem 126 protrudes downwardly from external stem 124, and sub-stem 128 protrudes downwardly from lower stem 126. First spring 130, second spring 132, and piston 134 are positioned around sub-stem 128.

As seen in FIGS. 8A, 8B, and 8C, a method of using the nasal spray bottle with improved nozzle according to present invention 10 comprises the steps of:

A) positioning head H of user U at approximately 90 degrees;

B) placing nozzle body 52 at application angle β between about 12 and 45 degrees to head H;

C) introducing nozzle body 52 approximately 1.5 cm inside nostril N of user U;

D) pressing actuator tabs 62 two times into each nostril N.

The application angle s used for present invention 10 is between 12 and 45 degrees. This allows an angle of dispersions δ between about 73.3 to 80.5 degrees. This open angle generates a swearing effect allowing an improved medication M target delivery.

Table 1 shows results of a study on users U for spray patterns and plume geometry using present invention 10 and its application system.

TABLE 1

| Samples | Samples | SP 30 mm | | | | PG 30 mm | | | |
|---|---|---|---|---|---|---|---|---|---|
| Lot # | # | Area | | Ovality ratio | | Angle | | Width | |
| Present invention 10 | 1 | 1764.3 | 1816.1 | 1.311 | 1.309 | 72.5 | 73.7 | 44.09 | 45.11 |
| | | 1828.9 | | 1.3 | | 75.8 | | 46.77 | |
| | | 1855 | | 1.317 | | 72.8 | | 44.47 | |
| | 2 | 2008.8 | 1917.3 | 1.395 | 1.394 | 81.9 | 80.5 | 52.14 | 50.99 |
| | | 1868.2 | | 1.376 | | 82.8 | | 52.9 | |
| | | 1874.8 | | 1.412 | | 76.8 | | 47.92 | |
| | 3 | 2212.9 | 2346.4 | 1.225 | 1.187 | 80.1 | 80.1 | 50.6 | 50.60 |
| | | 2392.3 | | 1.168 | | 80.2 | | 50.6 | |
| | | 2433.9 | | 1.167 | | 80.1 | | 50.6 | |
| | 4 | 2091.2 | 2099.1 | 1.356 | 1.332 | 76.6 | 76.7 | 47.92 | 48.30 |

TABLE 1-continued

| Samples Lot # | Samples # | SP 30 mm | | | | PG 30 mm | | | |
|---|---|---|---|---|---|---|---|---|---|
| | | Area | | Ovality ratio | | Angle | | Width | |
| | | 2106.4 | | 1.287 | | 71 | | 44.09 | |
| | | 2099.8 | | 1.353 | | 82.4 | | 52.9 | |
| | 5 | 2021.1 | 1963.5 | 1.218 | 1.255 | 72.1 | 73.3 | 43.7 | 44.72 |
| | | 1930.4 | | 1.279 | | 74.6 | | 46 | |
| | | 1939 | | 1.268 | | 73.1 | | 44.47 | |
| Minimum value | | 1816.1 | | 1.187 | | 73.3 | | 44.72 | |
| Maximal value | | 2346.4 | | 1.394 | | 80.5 | | 50.99 | |
| Average | | 2028.5 | | 1.295 | | 76.9 | | 47.94 | |

Table 2 shows results of a study on users U for spray patterns and plume geometry of conventional applications of prior art nozzles.

TABLE 2

| Samples Lot # | Samples # | SP 30 mm | | | | PG 30 mm | | | |
|---|---|---|---|---|---|---|---|---|---|
| | | Area | | Ovality ratio | | Angle | | Width | |
| Commercially Available Nozzles | 1 | 923.2 | 938.6 | 1.173 | 1.155 | 68.1 | 69.2 | 40.62 | 41.51 |
| | | 963.6 | | 1.141 | | 70 | | 42.15 | |
| | | 929.1 | | 1.15 | | 69.6 | | 41.77 | |
| | 2 | 928.8 | 927.7 | 1.256 | 1.224 | 71.4 | 70.3 | 43.3 | 42.41 |
| | | 914.3 | | 1.242 | | 70 | | 42.15 | |
| | | 940 | | 1.173 | | 69.4 | | 41.77 | |
| | 3 | 929.2 | 935.7 | 1.195 | 1.193 | 69 | 70.3 | 41.38 | 42.41 |
| | | 929.5 | | 1.212 | | 69.6 | | 41.77 | |
| | | 948.3 | | 1.171 | | 72.3 | | 44.07 | |
| | 4 | 793.8 | 784.6 | 1.388 | 1.390 | 66.1 | 65.1 | 39.09 | 38.32 |
| | | 783 | | 1.407 | | 66.6 | | 39.47 | |
| | | 777.1 | | 1.376 | | 62.5 | | 36.4 | |
| | 5 | 769.1 | 764.6 | 1.37 | 1.381 | 66.9 | 66.7 | 39.85 | 39.60 |
| | | 764.3 | | 1.393 | | 66 | | 39.09 | |
| | | 760.4 | | 1.379 | | 67.1 | | 39.85 | |
| Minimum value | | 764.6 | | 1.155 | | 65.1 | | 38.32 | |
| Maximal value | | 938.6 | | 1.390 | | 70.3 | | 42.41 | |
| Average | | 870.2 | | 1.268 | | 68.3 | | 40.85 | |

The studies show that a spray plume geometry angle of dispersions δ using present invention 10 is an open-angle between 73.3 to 80.5 degrees having an average of 76.9 degrees, and the spray plume geometry angle of dispersions δ using prior art nozzles is a narrow angle between 65.1 to 70.3 degrees having an average of 68.3 degrees.

The spray plume geometry angle of dispersions δ between about 73.3 to 80.5 degrees is an open-angle proving by present invention 10, which allow an excellent medication M target delivery (DTD) without the side effects of the narrow angle nozzles of prior art.

Nozzle body 52 is placed in application angle β between about 12 and 15 degrees for the treatment of viral diseases and vaccines applications. Nozzle body 52 applied at application angle β between about 12 and 15 degrees guarantee an eighth-fold increase in the medication M target delivered to the nasopharynx and upper oropharyngeal area, where the largest concentration of receptors where viruses are attached is located. In a preferred embodiment, nasal spray bottle according to present invention 10 is placed in application angle β of 15 degrees for the treatment of viral diseases and vaccines applications.

In addition, nozzle body 52 is placed at application angle β of approximately 45 degrees to target the area in nasal passages where nozzle body 52 provides the best medication M target delivery for treating rhinitis and sinusitis.

Present invention 10 overcomes structural limitations of the current conventional nasal delivery due to the dynamics of nozzle body 52 having flap guidance 60, which may translate into clinical benefit for users U. Present invention 10 spreads medication M particles evenly in nostrils N. Hence, the risk of rhinitis medicinal induced by shearing pressure and poor medication M distribution generated by traditional nozzles is significantly reduced. Additionally, the application of present invention 10 have been tested using an application angle β of approximately 15 degrees based on the optimal parameters for targeting the nasopharynx where most of the SARS-CoV2, Influenza, and others viral particles are concentrated. Also effective for the application of intranasal vaccines.

Present invention 10 comprises the following benefits to users U when used for the indication of viral illness.
Easy instructions for safe and practical application of the atomizer.
Atomizer with the ability to evenly distribute particles while minimizing pressure and irritation to users U.
The indicated application angle β of approximately 15 degrees to maximize medication M delivery on the nasopharynx, which is the target size of viral infection.

EXAMPLES

Example 1

Use and Efficacy of Present Invention 10.
Tests performed on the nozzle with saline, and multiple active ingredients and conclusions of the value of the new nozzle.
Droplet Size Distribution (DSD)
Droplet size measurement of the dispersed aerosol was measured by laser diffraction. The nasal spray according present invention 10 was actuated at 3 from the laser in a carefully defined position with an extraction hood on top to ensure safety of the analyst.
Spray Content Uniformity (SCU)
Spray content uniformity was performed as stipulated for nasal medication M products in the USP and FDA guidance. The measure of the mass was taken before and after the actuation of the device.
Spray Pattern (SP) and Plume Geometry Analysis (PG)
The spray pattern and plume geometry were evaluated by a pulsed laser plane that is cut and lighted horizontally while a high-speed imaging was being recorded. The laser plan was positioned at 3 and 6 cm from the nozzle. All formulations presented similar spray pattern, suggesting that the device is the key factor influencing this parameter.
Droplet Size Distribution (DSD) Method Development
The evaluation of the Droplet size will ensure placement of the active ingredient of desired dosage at the intended place of absorption. The DSD should be in the following range: 30-120 μm. Minimum V % below 5 μm. Droplets that are too large (>120 μm) can deposit mainly in the anterior parts of the nose. If the droplets are too small (<10 μm), they can possibly be inhaled and reach the lungs.

The data reported should be collected only during the fully developed phase as per US guidance. Six analyses were performed and the data was compared as presented in. These data suggest that selecting the time frame corresponding to the average of the time at 90% of the maximum obscuration is an appropriate method to select the fully developed phase. This phase was defined as the phase within 0.121-0.208 s and the average of the droplet size distribution during this phase should be performed for each run.

Figure 9:
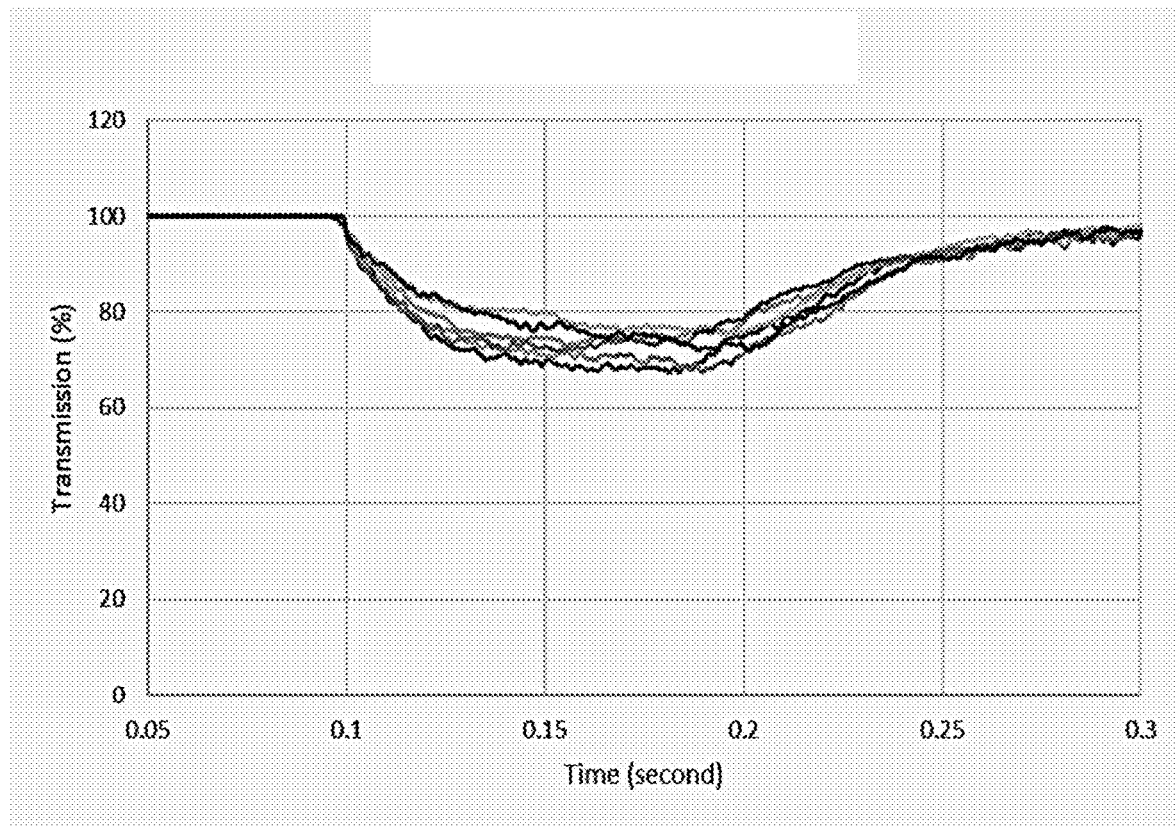
FIG. 9 is a graphic showing droplet size distribution.

As seen in FIG. 9, the droplet size distribution is within the expected range for nasal delivery (10-120 μm) with a minor percentage of droplets below 5 μm, enhanced by the open angle swirling effect.

Conclusion:

1. Spray Content Uniformity (SCU), Spray Pattern (SP) met the FDA requirements. The Plume Geometry analysis (PG) shows that the spray plume geometry angle of dispersions δ is between about 73 to 80.5 degrees that generates a swearing effect with excellent medication M target delivery (DTD) without the side effects of the narrow angle nozzles that dominate the market.

2. An open-angle swirling effect atomizer according to present invention 10 generate a swirling effect by opening a spray cone from a tapered nozzle bottle to determine the most efficient one to enhance medication M delivery and aid in patient compliance.

3. A rotary atomization nasal medication M delivery system was mainly aimed at solving the disadvantages of the existing nasal medication M delivery device, such as causing nasal discomfort to patients and that it cannot ensure that the liquid reaches the accurate medication M delivery position, and hence failing to achieve the desired efficacy. According to the nasal aerodynamics principle, the rotary atomizing nasal cavity is designed as a special structure in the injector nozzle. It is atomized into a rotating column before the liquid spray, and a hollow wide-angle cone shape is formed after the liquid spray is discharged. According to the medicine's characteristics and the treatment requirement, the size of the spray particle is fixed, the spray shape and the spray angle are determined to ensure that the sprayed medication M is not made to the mucous membrane. It can also enhance the intranasal transmission of spray particles to achieve adequate medication M distribution.

Example 2

Efficacy of the use of present invention 10 according to the spray pattern, plume geometry, and droplets size.

Studies of nasal spray formulations containing Chlorpheniramine maleate (CPM) and multiple excipients such as xylitol, sorbitol, erythritol, sucralose, glycerin, Ethylenediaminetetraacetic acid (EDTA), fluticasone, and others are performed using a 15 ml bottle according to present invention 10.

The studies were performed to test spray pattern, plume geometry, and droplets size.

Spray Pattern (SP) and Plume Geometry Analysis (PG)

The spray pattern and plume geometry were evaluated by a pulsed laser plane that is cut and lighted horizontally while a high-speed imaging was being recorded. The laser plan was positioned at 3 and 6 cm from the nozzle.

Spray pattern testing was performed at two distances (3 and 6 cm), and the results revealed that with increasing distance, there is an increase in the spray pattern area for all formulations with an increase on the ovality ratio. It has been previously concluded that a uniform circular plume with an ovality ratio close to one can be considered ideal. All formulations presented similar spray pattern, suggesting that the device is the key factor influencing this parameter.

Table 3 shows spray pattern average (n=3) summary results for NP-175-458-002, NP-175-20458-003 and NP-175-20458-004 at 3 cm and 6 cm.

TABLE 3

| Formulation ID | Xylitol substitute (% w/w) | Time point (weeks) | Conditions | Distance (cm) | Dmin (cm) | Dmax (cm) | Ovality ratio | Area (cm2) |
|---|---|---|---|---|---|---|---|---|
| NP-175-20458-002 | Sorbitol 2.5% | 0 | 40° C./ 75% RH | 3 | 5.30 ± 0.29 | 6.94 ± 0.43 | 1.31 ± 0.01 | 28.95 ± 3.43 |
|  |  |  |  | 6 | 7.25 ± 0.24 | 11.4 ± 0.74 | 1.58 ± 0.10 | 65.02 ± 5.23 |
|  |  | 2 |  | 3 | 5.42 ± 0.14 | 7.14 ± 0.34 | 1.32 ± 0.07 | 30.39 ± 1.58 |
|  |  |  |  | 6 | 8.00 ± 0.78 | 14.64 ± 0.37 | 1.84 ± 0.16 | 92.10 ± 10.64 |
|  |  | 4 |  | 3 | 5.06 ± 0.30 | 6.66 ± 0.07 | 1.32 ± 0.08 | 26.46 ± 1.56 |
|  |  |  |  | 6 | 7.40 ± 0.51 | 15.47 ± 0.41 | 2.10 ± 0.14 | 89.89 ± 7.37 |
| NP-175-20458-003 | Dextrose anhydrous 3.0% | 0 |  | 3 | 5.15 ± 0.08 | 6.42 ± 0.26 | 1.25 ± 0.05 | 25.94 ± 1.25 |
|  |  |  |  | 6 | 8.09 ± 0.45 | 12.47 ± 0.40 | 1.55 ± 0.11 | 79.26 ± 4.78 |
|  |  | 2 |  | 3 | 5.54 ± 0.26 | 7.29 ± 0.39 | 1.32 ± 0.05 | 31.77 ± 2.90 |
|  |  |  |  | 6 | 8.30 ± 0.56 | 14.42 ± 1.12 | 1.74 ± 0.04 | 94.29 ± 13.66 |
|  |  | 4 |  | 3 | 4.97 ± 0.25 | 6.86 ± 0.21 | 1.38 ± 0.06 | 26.78 ± 1.95 |
|  |  |  |  | 6 | 7.39 ± 0.36 | 15.94 ± 0.76 | 2.16 ± 0.04 | 92.67 ± 8.64 |
| NP-175-20458-004 | Mannitol 2.7% | 0 |  | 3 | 4.91 ± 0.21 | 6.43 ± 0.41 | 1.31 ± 0.08 | 24.82 ± 2.20 |
|  |  |  |  | 6 | 8.76 ± 0.49 | 12.44 ± 0.43 | 1.42 ± 0.04 | 85.63 ± 7.48 |
|  |  | 2 |  | 3 | 5.17 ± 0.15 | 7.43 ± 0.10 | 1.44 ± 0.03 | 30.21 ± 1.24 |
|  |  |  |  | 6 | 7.92 ± 0.42 | 14.09 ± 0.03 | 1.78 ± 0.09 | 87.65 ± 4.65 |
|  |  | 4 |  | 3 | 4.38 ± 0.33 | 7.06 ± 0.13 | 1.62 ± 0.14 | 24.27 ± 1.72 |
|  |  |  |  | 6 | 6.65 ± 0.15 | 14.5 ± 0.82 | 2.18 ± 0.12 | 75.72 ± 5.08 |

For plume geometry measurements, the laser sheet was oriented vertically along the long axis of the nasal spray device, and the plume was imaged from the side, directly above the device tip. Again, the formulation impact on the plume geometry appeared to be minimal.

Table 4 shows plume Geometry average (n=3) summary results for NP-175-458-002, NP-175-20458-003 and NP-175-20458-004.

TABLE 4

| Formulation ID | Xylitol substitute (% w/w) | Time point (weeks) | Conditions | Plume angle (*) | Length (cm) | Plume width (cm) |
|---|---|---|---|---|---|---|
| NP-175-20458-002 | Sorbitol 2.5% | 0 | 40 C./ 75% RH | 123.50 ± 7.27 | 12.07 ± 0.95 | 12.61 ± 0.99 |
|  |  | 2 |  | 108.65 ± 3.38 | 12.99 ± 0.44 | 13.37 ± 0.20 |
|  |  | 4 |  | 114.58 ± 0.82 | 13.55 ± 0.50 | 7.41 ± 0.45 |
| NP-175-20458-003 | Dextrose anhydrous 3.0% | 0 |  | 118.74 ± 4.52 | 11.42 ± 0.83 | 11.9 ± 1.20 |
|  |  | 2 |  | 115.79 ± 2.93 | 11.14 ± 0.21 | 13.14 ± 0.46 |
|  |  | 4 |  | 117.26 ± 8.39 | 13.38 ± 0.62 | 7.87 ± 0.69 |
| NP-175-20458-004 | Mannitol 2.7% | 0 |  | 105.62 ± 2.43 | 12.16 ± 0.09 | 11.59 ± 0.72 |
|  |  | 2 |  | 113.09 ± 2.90 | 11.85 ± 0.35 | 9.82 ± 0.98 |
|  |  | 4 |  | 128.82 ± 10.46 | 13.73 ± 0.88 | 9.94 ± 0.90 |

The droplet size distribution of the dispersed aerosol was measured by laser diffraction. Laser diffraction is a fast and efficient method that measures the geometric size of droplets and particles in real time based on two common light scattering principles, which are Mie or Fraunhofer-theory. The nasal spray was actuated at 3 cm from the laser in a carefully defined position with an extraction hood on top to ensure safety of the analyst. The DSD and obscuration were recorded at a frequency of 2.5 kHz for 0.6 s after the transmission dropped below 98%, while capturing the 0.1 s before dropping to this value. On the basis of time history profiles, the spray event can be characterized in three phases:

The formation phase, which is indicated by a rapid increase in obscuration and decrease in droplet size;

Fully developed phase, where the obscuration and droplet size attain a plateau;

Dissipation phase, with a rapid decrease in obscuration and increase in droplet size.

The data reported should be collected only during the fully developed phase as per US guidance. Therefore, to determine the fully developed phase, six analyses were performed and the data was compared as presented in. These data suggest that selecting the time frame corresponding to the average of the time at 90% of the maximum obscuration is an appropriate method to select the fully developed phase.

Table 5 shows average droplet size distribution (n=3) summary results for NP-175-458-002, NP-175-20458-003 and NP-175-20458-004 at different stability time points.

TABLE 5

| Formulation ID | Xylitol substitute (% w/w) | Time point (weeks) | Conditions | Dv10 (µm) | Dv50 (µm) | Dv90 (µm) | % <5 µm |
|---|---|---|---|---|---|---|---|
| NP-175-20458-002 | Sorbitol 2.5% | 0 | 40° C./ 75% RH | 21.85 ± 1.66 | 43.30 ± 2.29 | 104.06 ± 5.98 | 0.41 ± 0.36 |
|  |  | 2 |  | 22.80 ± 0.61 | 49.72 ± 2.83 | 105.54 ± 5.18 | 0.47 ± 0.11 |
|  |  | 4 |  | 19.51 ± 0.33 | 42.36 ± 0.97 | 108.84 ± 2.38 | 0.12 ± 0.13 |
| NP-175-20458-003 | Dextrose anhydrous 3.0% | 0 |  | 20.65 ± 0.59 | 43.84 ± 2.64 | 105.00 ± 2.65 | 0.59 ± 0.61 |
|  |  | 2 |  | 22.25 ± 2.10 | 50.74 ± 4.35 | 118.78 ± 11.58 | 0.34 ± 0.33 |
|  |  | 4 |  | 19.55 ± 0.45 | 37.94 ± 0.90 | 82.81 ± 4.93 | 0.23 ± 0.20 |
| NP-175-20458-004 | Mannitol 2.7 % | 0 |  | 19.36 ± 0.48 | 39.47 ± 1.14 | 89.14 ± 7.63 | 0.51 ± 0.41 |
|  |  | 2 |  | 20.56 ± 0.50 | 41.24 ± 1.80 | 88.25 ± 5.55 | 0.06 ± 0.10 |
|  |  | 4 |  | 20.62 ± 0.55 | 40.80 ± 1.35 | 96.07 ± 5.12 | 0.00 ± 0.00 |

Conclusions

The spray content uniformity met the FDA requirements for all formulations and result in a delivered dose around 400 µg of CPM per spray.

The droplet size distribution is within the expected range for nasal delivery (10-120 µm) with a minor percentage of droplets below 5 µm. These data suggest that lung safety studies should not be required.

Spray pattern and plume geometry testing demonstrated minimal influence of the formulation on the results, suggesting that the device is the key factor influencing these parameters.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A nasal spray bottle with improved nozzle, comprising:
A) a cap assembly;
B) a nozzle assembly having a flap guidance attached around a nozzle body defining a predetermined angle between 30 and 60 degrees respect to a bottle bottom base, said nozzle assembly A further comprises actuator tabs, a lower wall, and the nozzle body having a nozzle top end and a nozzle bottom end, whereby said nozzle top end comprises an orifice;
C) a bottle coupling assembly comprising a coupling upper wall, a coupling lower wall, a bottom end defining a lower lip, an internal wall having a top wall defining a hole, a chaplet, and a gasket below said chaplet;
D) a dispenser mechanism; and
E) a bottle assembly, wherein said nozzle assembly couples to said bottle coupling assembly, said bottle coupling assembly mounts onto said bottle assembly, and said dispenser mechanism is inside along said nozzle assembly, said bottle coupling assembly, and said bottle assembly.

2. The nasal spray bottle with improved nozzle set forth in claim 1, wherein said cap assembly comprises a cap upper section, a cap lower section, a bottom end, and a top end.

3. The nasal spray bottle with improved nozzle set forth in claim 1, wherein said flap guidance comprises first and second transversal edges, first and second longitudinal edges, and a central edge.

4. The nasal spray bottle with improved nozzle set forth in claim 3, wherein said flap guidance is fixedly attached around said nozzle body by said central edge.

5. The nasal spray bottle with improved nozzle set forth in claim 3, wherein said first transversal edge approximately aligns with said nozzle bottom end and said second transversal edge is separated a predetermined distance from said nozzle bottom end toward said nozzle top end.

6. The nasal spray bottle with improved nozzle set forth in claim 1, wherein said flap guidance is oval shaped.

7. The nasal spray bottle with improved nozzle set forth in claim 1, wherein said flap guidance allow a user to orientate said nozzle body in a predetermined application angle between 12 to 45 degrees.

8. The nasal spray bottle with improved nozzle set forth in claim 7, wherein said nozzle assembly is configured with a plume geometry swirling effect that delivers an angle of dispersion between 73.3 to 80.5 degrees.

9. A method of using the nasal spray bottle with improved nozzle set forth in claim 8, comprising the steps of:
　A) positioning a head of said user in approximately 90 degrees;
　B) placing said nozzle body at said application angle between 12 and 45 degrees to said head;
　C) introducing said nozzle body approximately 1.5 cm inside a nostril of said user;
　D) pressing said actuator tabs 2 times into each nostril.

10. A method of using the nasal spray bottle with improved nozzle set forth in claim 9, wherein said application angle allows said angle of dispersion between 73.3 to 80.5 degrees.

11. A method of using the nasal spray bottle with improved nozzle set forth in claim 9, wherein said nozzle body is placed in said application angle between 12 and 15 degrees for the treatment of viral diseases and vaccines applications, and approximately 45 degrees for the treatment of allergic rhinitis.

12. The nasal spray bottle with improved nozzle set forth in claim 1, wherein said chaplet is inside said internal walls, and said coupling upper wall and said internal wall define an elongated channel to receive said lower wall.

13. The nasal spray bottle with improved nozzle set forth in claim 1, wherein said dispenser mechanism comprises an inner stem to create a swirling effect, an external stem, a lower stem, a sub-stem, first and second springs, a piston, a housing, a ball, and a tube.

14. The nasal spray bottle with improved nozzle set forth in claim 13, wherein said housing houses said sub-stem, said first and second springs, said piston, and said ball, and said chaplet receives said housing, whereby said tube protrudes from said housing toward said bottle bottom base.

15. The nasal spray bottle with improved nozzle set forth in claim 1, wherein said bottle assembly comprises a bottle neck, a bottle top end, external threads, a neck tab, and a bottle body.

16. The nasal spray bottle with improved nozzle set forth in claim 15, wherein said coupling lower wall comprises internal threads to receive said external threads and said gasket is positioned between said chaplet and said bottle top end.

\* \* \* \* \*